(12) United States Patent
Stanislawczyk et al.

(10) Patent No.: US 12,102,356 B2
(45) Date of Patent: Oct. 1, 2024

(54) REMOVAL TOOL FOR A SUBCUTANEOUS IMPLANTABLE DEVICE

(71) Applicant: Senseonics, Incorporated, Germantown, MD (US)

(72) Inventors: Christopher Stanislawczyk, Germantown, MD (US); Philip Huffstetler, Germantown, MD (US); Bryan Hays, Germantown, MD (US); Lynne Kelley, Germantown, MD (US); Sanat Mohanty, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 810 days.

(21) Appl. No.: 16/926,438

(22) Filed: Jul. 10, 2020

(65) Prior Publication Data
US 2021/0007780 A1 Jan. 14, 2021

Related U.S. Application Data

(60) Provisional application No. 62/872,876, filed on Jul. 11, 2019.

(51) Int. Cl.
*A61B 17/52* (2006.01)
*A61B 5/145* (2006.01)
(Continued)

(52) U.S. Cl.
CPC ............ *A61B 17/52* (2013.01); *A61B 5/1451* (2013.01); *A61B 5/14532* (2013.01);
(Continued)

(58) Field of Classification Search
CPC ... A61B 17/52; A61B 5/1451; A61B 5/14532; A61B 17/32093; A61B 2017/00367;
(Continued)

(56) References Cited

U.S. PATENT DOCUMENTS 9,551,863 B2 * 1/2017 Lyons ................ G02B 23/2476
2014/0243587 A1 * 8/2014 Rohaninejad ........ A61B 17/122
600/37
(Continued)

FOREIGN PATENT DOCUMENTS

EP 3017778 A1 * 5/2016
EP 3545897 A1 * 10/2019 ......... A61B 17/3468

OTHER PUBLICATIONS

Reddit Website, https://www.reddit.com/r/techsupportmacgyver/comments/55g91d/by_popular_request_the_subdermal_magnet_implants/ (Year: 2016).*

*Primary Examiner* — Charles A Marmor, II
*Assistant Examiner* — Meghan R Kumar
(74) *Attorney, Agent, or Firm* — Rothwell, Figg, Ernst & Manbeck, P.C.

(57) ABSTRACT

A removal tool uses magnetic attraction to guide the removal tool toward an implantable device subcutaneously implanted in subcutaneous tissue of a host and to remove the implantable device from the host. The removal tool may include first and second lever members that are pivotably connected together, and the first and second lever members include a pair of jaw members configured to move between open and closed positions to grasp the implantable device. The first jaw member may include a magnet to magnetically attract and couple to an implantable device implanted subcutaneously below a skin surface of a host.

31 Claims, 14 Drawing Sheets

(51) Int. Cl.
*A61B 17/00* (2006.01)
*A61B 17/3209* (2006.01)
(52) U.S. Cl.
CPC .................... *A61B 17/32093* (2013.01); *A61B 2017/00367* (2013.01); *A61B 2560/06* (2013.01)
(58) Field of Classification Search
CPC ............ A61B 2560/06; A61B 17/3468; A61B 2017/2901; A61B 17/2804; A61B 17/282; A61B 2017/00876
See application file for complete search history.

(56) References Cited

U.S. PATENT DOCUMENTS

2015/0359553 A1* 12/2015 Harnisch ................ A61N 1/372
 606/210
2017/0065369 A1* 3/2017 Bornzin .................. A61B 5/29

* cited by examiner

REMOVAL TOOL FOR A SUBCUTANEOUS IMPLANTABLE DEVICE

CROSS-REFERENCE TO RELATED APPLICATION

The present application claims the benefit of priority to U.S. Provisional Application Ser. No. 62/872,876, filed on Jul. 11, 2019, which is incorporated herein by reference in its entirety.

BACKGROUND

Field of Invention

The present disclosure relates to a removal tool for a subcutaneous implant device and a method of using the removal tool to remove the subcutaneous implant device from a host.

Discussion of the Background

Implantable devices, such as sensors, may be implanted within a living animal (e.g., a human) and may detect the presence or amount of an analyte (e.g., glucose or oxygen) in a medium (e.g., blood or interstitial fluid) within the living animal. Some implantable devices are relatively small (e.g., 2-4 mm diameter capsule) and may be implanted in the subcutaneous tissue of a host by creating a small incision in the skin surface.

After a period of time, implantable devices may need to be retrieved from a host for various reasons, such as for example, replacing a battery in the implantable device or replacing a deteriorated implantable device with a new implantable device. Due to the small size of the implantable device, it may be difficult to locate and retrieve the implantable device out of the subcutaneous tissue of the host.

SUMMARY

The present invention overcomes the disadvantages of prior systems by providing, among other advantages, a removal tool that reliably locates the position of the implantable device subcutaneously implanted beneath the skin surface of a host through the use of magnetic attraction between the removal tool and the implantable device. In some embodiments, the present invention may provide an improved removal tool that uses magnetic force to slide or dislodge the implantable device from the pocket in the tissue of the host to effectively remove the implantable device from the host.

One aspect of the invention may provide a removal tool. The removal tool may include a first lever member comprising a first handle at a first end thereof and a first jaw member at a second end thereof. The removal tool may include a second lever member comprising a second handle at a first end thereof and a second jaw member at a second end thereof. The first lever member may be pivotably coupled to the second lever member at a joint such that the first and second jaw members are configured to move between a closed position in which the first jaw member abuts against the second jaw member and an open position in which the first jaw member is spatially separated from the second jaw member. The first jaw member may comprise a magnet configured to magnetically attract and couple to an implantable device implanted subcutaneously below a skin surface of a host.

Another aspect of the invention may provide a method for removing an implantable device implanted subcutaneously in a tissue pocket below a skin surface of a host. The method may include a step (a) of inserting a first jaw member of a first lever member of a removal tool and a second jaw member of a second lever member of the removal tool into an incision in the skin surface. The method may include a step (b) of guiding the first jaw member and the second jaw member toward the implantable device using magnetic attraction of a magnet of the first jaw member and the implantable device. The method may include a step (c) of grasping the implantable device between the first and second jaw members. The method may include a step (d) of removing the first and second jaw members and the implantable device grasped between the first and second jaw members out of the tissue pocket and through the incision.

Still another aspect of the invention may provide a removal tool. The removal tool may include a rod including a handle at a proximal end of the rod. The removal tool may include a cup disposed at a distal end of the rod, wherein the cup includes a base and a sidewall projecting from the base. The removal tool may include a magnet disposed in the cup and coupled to the base. The magnetic may be configured to magnetically attract and couple to an implantable device implanted subcutaneously below a skin surface of a host.

Yet another aspect of the invention may provide a method for removing an implantable device implanted subcutaneously in a tissue pocket below a skin surface of a host. The method may include a step (a) of inserting a cup disposed at a distal end of a rod of a removal tool into an incision in the skin surface. The method may include a step (b) of guiding the cup toward the implantable device using magnetic attraction of a magnet and the implantable device, wherein the magnet is disposed in the cup and coupled to a base of the cup. The method may include a step (c) of holding the implantable device in the cup using magnetic coupling of the implantable device and the magnet. The method may include a step (d) of removing the cup and the implantable device held in the cup out of the tissue pocket and through the incision.

Still another aspect of the invention may provide a removal tool. The removal tool may include a rod including a handle at a proximal end of the rod. The removal tool may include a cup disposed at a distal end of the rod, wherein the cup includes a base and a sidewall projecting from the base. The removal tool may include a coil disposed in the cup and coupled to the base. The removal tool may include circuitry in electrical communication with the coil. The circuitry may be configured to generate and apply a current to the coil, such that the coil generates an electromagnetic field that magnetically attracts the coil and the implantable device.

Yet another aspect of the invention may provide a method for removing an implantable device implanted subcutaneously in a tissue pocket below a skin surface of a host. The method may include a step (a) of inserting a cup disposed at a distal end of a rod of a removal tool into an incision in the skin surface. The method may include a step (b) of using circuitry of the removal tool to apply a current to a coil of the cup of the removal tool, wherein application of the current to the coil generates an electromagnetic field that attracts the coil and the implantable device, guides the cup toward the implantable device, and holds the implantable device in the cup. The method may include a step (c) of removing the cup and the implantable device held in the cup out of the tissue pocket and through the incision.

Still another aspect of the invention may provide a method for removing an implantable device implanted subcutaneously in a tissue pocket below a skin surface of a host. The method may include a step (a) of creating an incision in the skin surface. The method may include a step (b) of placing a magnet on the skin surface above the implantable device, wherein the magnet attracts the implantable device. The method may include a step (c) of moving the magnet toward the incision, wherein movement of the magnet toward the incision moves the implantable device toward the incision. The method may include a step (d) of moving the magnet past the incision, wherein movement of the magnet past the incision moves the implantable device out of the tissue pocket and through the incision.

Yet another aspect of the invention may provide a removal tool including a first lever member, a second lever member, and a rod. The first lever member may include a first handle at a first end of the first lever member and an actuator at a second end of the first lever member. The second lever member may include a second handle at a first end of the second lever member and a first jaw member at a second end of the second lever member. The rod may include a contact portion at a first end of the rod and a second jaw member at a second end of the rod. The actuator of the first lever member may be configured to contact the contact portion of the rod. The first lever member may be pivotably coupled to the second lever member at a joint such that the first and second handles are configured to move between an open position in which the first and second handles are relatively far from each other and a closed position in which the first and second handles are relatively close to each other. Movement of the first and second handles from the open position to the closed position may be configured to move the second jaw member from a retracted position to the extended position.

In some embodiments, the second lever member may further include an upper portion between the second handle and the joint and a lower portion between the joint and the first jaw member. In some embodiments, the lower portion of the second lever member may include a curved portion near the joint. In some embodiments, the rod may be parallel to the lower portion of the second lever member. In some embodiments, the lower portion of the second lever member may include one or more holders, and the rod may pass through the one or more holders.

In some embodiments, movement of the first and second handles between the open and closed positions may cause movement of the actuator, and movement of the actuator may cause movement of the rod. In some embodiments, the first and second jaw members may have a curved shape. In some embodiments, the first and second jaw members may together form a hollow cylindrical shape when the second jaw member is at the extended position. In some embodiments, the first and second jaw members may each have a shape that matches the shape of an implantable device. In some embodiments, the first and second jaw members may each have sharp end configured to dissect tissue attached to an implantable device.

Still another aspect of the invention may provide a method of using a removal tool. The method may include moving first and second handles of the removal tool from an open position in which the first and second handles are relatively far from each other to a closed position in which the first and second handles are relatively close each other. The first handle may be at a first end of a first lever member, an actuator may be at a second end of the first lever member, the second handle may be at a first end of a second lever member, and a first jaw member may be at a second end of the second lever member. Movement of the first and second handles from the open position to the closed position may move a second jaw member from a retracted position to an extended position, the actuator may be contact with a contact portion of a rod at a first end of the rod, and the second jaw member may be at a second end of the rod.

In some embodiments, movement of the first and second handles from the open to the closed position may cause movement of the actuator, and the movement of the actuator may cause movement of the rod.

Yet another aspect of the invention may provide a method for removing an implantable device implanted subcutaneously in a tissue pocket below a skin surface of a host. The method may include inserting a first jaw member of the removal tool into an incision in the skin surface. The method may include moving the first jaw member to a position adjacent to a first side of the implantable device. The method may include moving a second jaw member of the removal tool to a position adjacent to a second side of the implantable device. The second side of the implantable device may be opposite the first side of the implantable device. Moving the second jaw member to the position adjacent to the second side may include moving first and second handles of the removal tool from an open position in which the first and second handles are relatively far from each other to a closed position in which the first and second handles are relatively close each other. Moving the first and second handles from the open position to the closed position may cause the second jaw member to move from a retracted position to an extended position, and the first and second jaw members may grasp the implantable device when in the positions adjacent to the first and second sides of the implantable device, respectively. The method may include removing the first and second jaw members and the implantable device grasped between the first and second jaw members out of the tissue pocket and through the incision.

In some embodiments, the method may further include creating the incision in a skin surface. In some embodiments, the first position adjacent to the first side of the implantable device may be below the implantable device, and the second position adjacent to the second side of the implantable device may be above the implantable device. In some embodiments, moving the first jaw member to the first position adjacent to the first side of the implantable device may include dissecting tissue attached to the first side of the implantable device. In some embodiments, moving the second jaw member to the second position adjacent to the second side of the implantable device may include dissecting tissue attached to the second side of the implantable device.

In some embodiments, the first handle may be at a first end of a first lever member, an actuator may be at a second end of the first lever member, the second handle may be at a first end of a second lever member, and moving the first and second handles from the open position to the closed position may cause movement of the actuator, which may cause movement of the second jaw member from the retracted position to the extended position. In some embodiments, the actuator may be in contact with a contact portion of a rod at a first end of the rod, and the second jaw member may be at a second end of the rod.

Yet another aspect of the invention may provide a method of removing an implantable device implanted subcutaneously in a tissue pocket below a skin surface of a host. The method may include placing a magnet on the skin surface above the implantable device. The magnet may attract the implantable device such that an outline of the implantable device is visible on the skin surface. The method may include creating an incision in the skin surface at one end of the outline of the implantable device created via the attraction of the implantable device and the magnet. The method may include removing the implantable device out of the tissue pocket and through the incision.

In some embodiments, the magnet may be configured to apply 2 to 4 pounds of magnetic force. In some embodiments, the magnet may be configured to apply a magnetic flux within the range of 0.45 T to 0.55 T. In some embodiments, removing the implantable device out of the tissue pocket and through the incision may include (i) inserting a first jaw member of a removal tool and a second jaw member of the removal tool into the incision in the skin surface; (ii) grasping the implantable device between the first and second jaw members; and (iii) removing the first and second jaw members and the implantable device grasped between the first and second jaw members out of the tissue pocket and through the incision.

These and other embodiments encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

Figure 1:
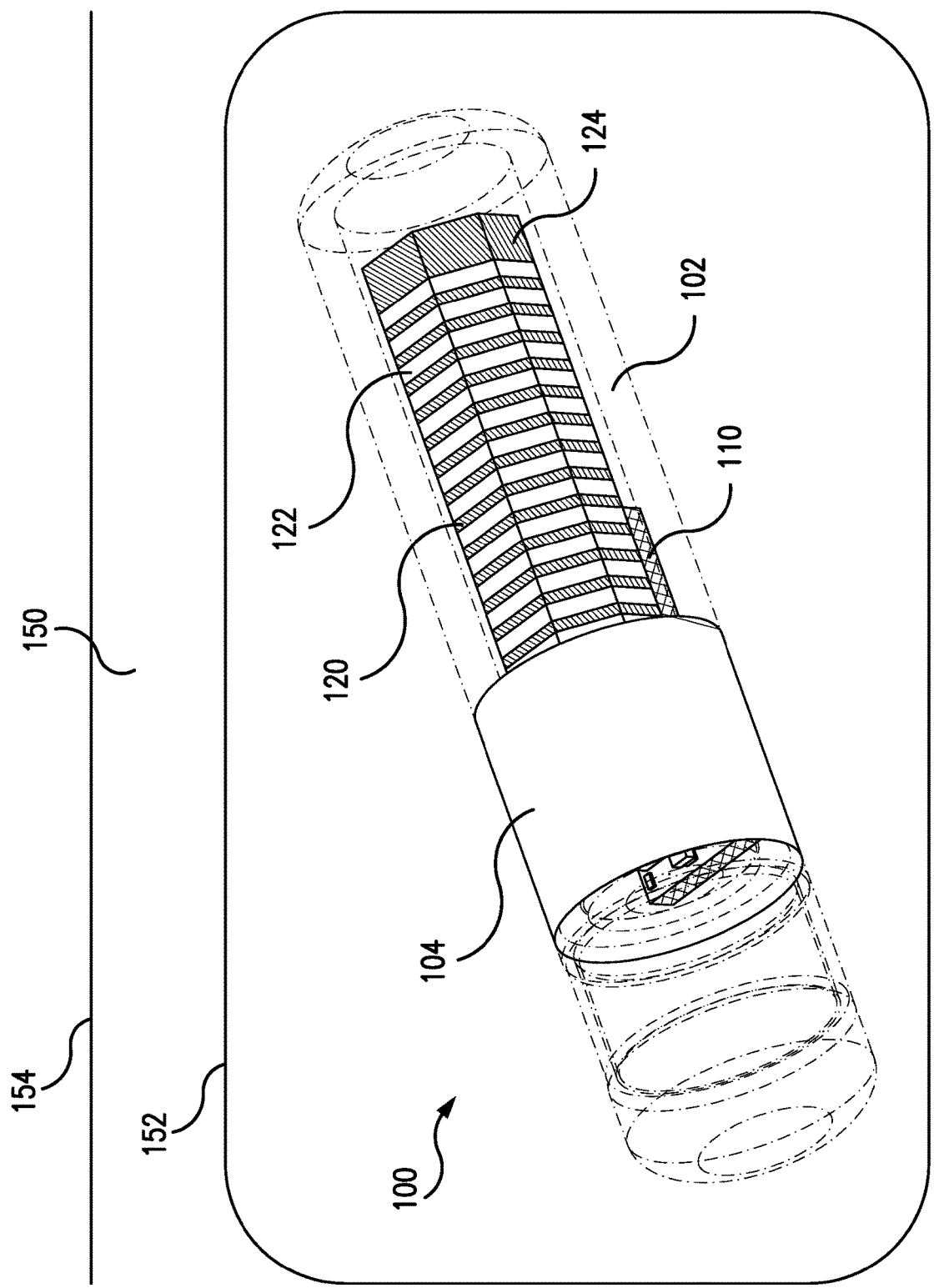
FIG. 1 is a perspective view illustrating a non-limiting example of an implantable device embodying aspects of the present invention.
Figure 2:
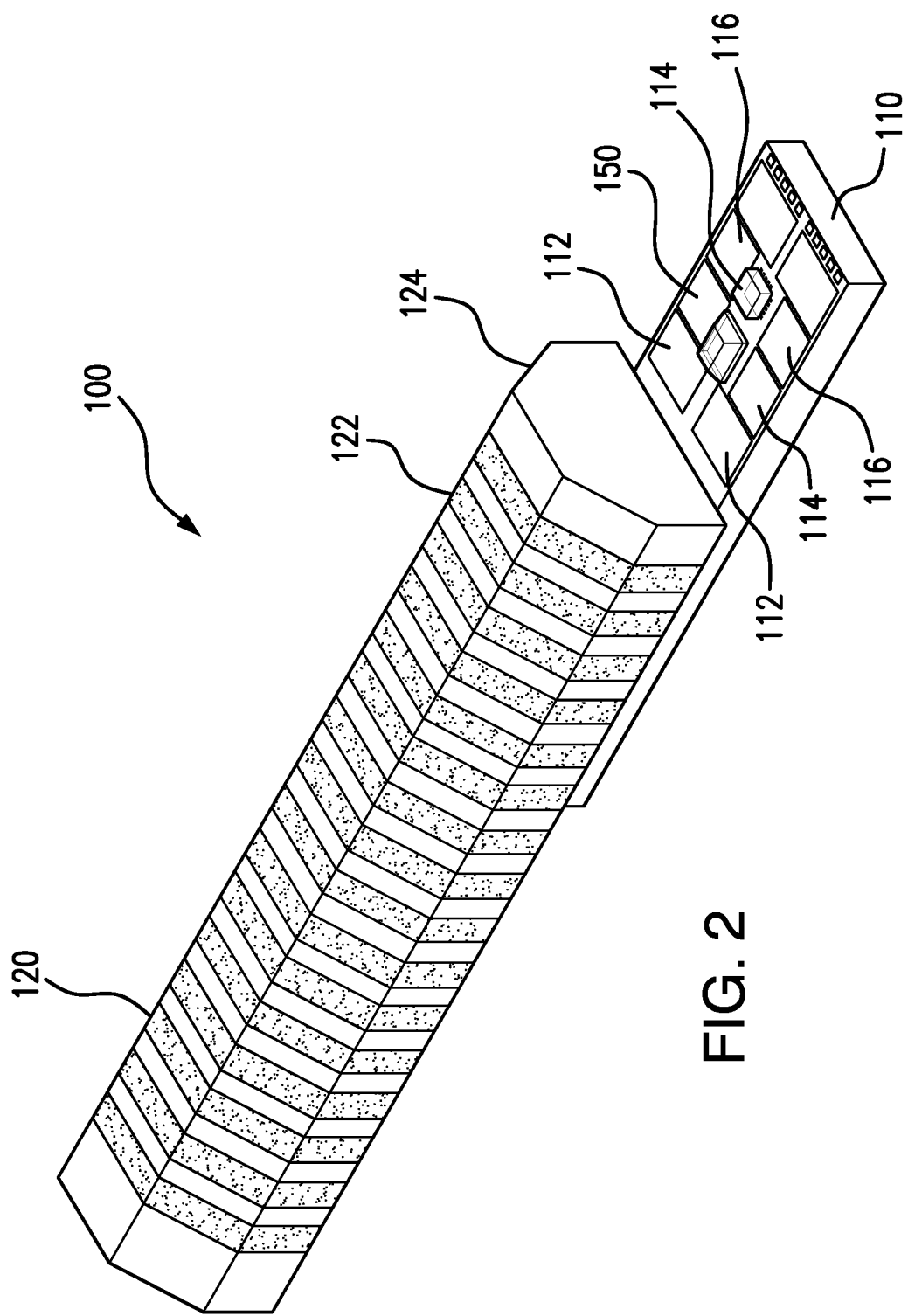
FIG. 2 is a perspective view illustrating elements of the non-limiting example of the implantable device embodying aspects of the present invention

FIG. 1 is a perspective view illustrating an exemplary implantable device 100 that may be used in an analyte monitoring system (e.g., a continuous glucose monitoring system) according to some non-limiting embodiments. FIG. 2 is a perspective view illustrating elements of the implantable device 100 according to some non-limiting embodiments. In some non-limiting embodiments, the implantable device 100 may be a small, fully subcutaneously implantable sensor, e.g., that measures the amount or concentration of an analyte (e.g., glucose) in a medium (e.g., interstitial fluid) of a living animal (e.g., a living human). In some alternative embodiments, the implantable device 100 is not a sensor and is instead a different type of implantable device, such as, for example and without limitation, an insulin pump, pacemaker, or electrical/heat therapy device.

In some non-limiting embodiments, as illustrated in FIG. 1, the implantable device 100 may be implanted in the tissue 150 (e.g., subcutaneous tissue) of the living animal, where the implantable device 100 may rest in a pocket 152 in the tissue 150 below the skin surface 154, and the pocket 152 may surround the implantable device 100. In some non-limiting embodiments, the pocket 152 may be created by a tissue dissector tool before implantation of the implantable device 100 or by the implantation process.

In some non-limiting embodiments, as illustrated in FIG. 1, the implantable device 100 may include a housing 102 (i.e., body, shell, capsule, or encasement), which may be rigid and biocompatible. In one non-limiting embodiment, the housing 102 may be a silicon tube. However, this is not required, and, in other embodiments, different materials and/or shapes may be used for the housing 102.

In some embodiments, as shown in FIG. 1, the implantable device 100 may include one or more analyte indicators 104, such as, for example, a polymer graft or hydrogel coated, diffused, adhered, embedded, or grown on or in at least a portion of the exterior surface of the housing 102. In some embodiments, the one or more analyte indicators 104 may be porous and may allow the analyte (e.g., glucose) in a medium (e.g., interstitial fluid) to diffuse into the one or more analyte indicators 104.

In some embodiments, the one or more indicator elements 104 (e.g., polymer grafts or hydrogels) of the implantable device 100 may include one or more indicator molecules (e.g., fluorescent indicator molecules). In some embodiments, the indicator molecules may produce (e.g., exhibit) one or more detectable properties (e.g., optical properties) that vary in accordance with the amount or concentration of the analyte in proximity to an analyte indicator 104. In some non-limiting embodiments, the indicator molecules may emit an amount of emission light (e.g., fluorescent light) that varies in accordance with the amount or concentration of the analyte in proximity to the analyte indicator 104.

In some embodiments, the implantable device 100 may include a substrate 110 (e.g., a printed circuit board (PCB) or flexible PCB), an internal excitation light source 111 mounted on the substrate 110, and one or more internal photodetectors 112, 114, and 116 mounted on the substrate 110. In some embodiments, the internal light source 111 may be configured to emit an excitation light over an excitation wavelength range that interacts with the one or more indicator molecules in the analyte indicator 104. In some embodiments, the internal photodetectors 112, 114, and 116 may include, for example, one or more photodiodes, phototransistors, photoresistors, or other photosensitive elements, that output a signal indicative of an amount of light received by the corresponding photodetector. In some examples, the signal output by the one or more internal photodetectors 112, 114, and 116 may be indicative of an amount or concentration of an analyte in a medium in proximity to the analyte indicator 104.

In some embodiments, as shown in FIGS. 1 and 2, the implantable device 100 may include an inductor 120, which may be, for example, a ferrite based micro-antenna. In some embodiments, the inductor 120 may include a conductor 122 in the form of a coil and a magnetic core 124. In some non-limiting embodiments, the core 124 may be, for example and without limitation, a ferrite core. In some embodiments, the inductor 120 may be connected to circuitry (e.g., an application specification integrated circuit (ASIC)) of the implantable device 100. In some embodiments, the inductor 120 may communicate with an external device (not shown) by, passive telemetry (e.g., near field communication), such that power and/or data is transferred between the implantable device 100 and the external device.

Figure 3:
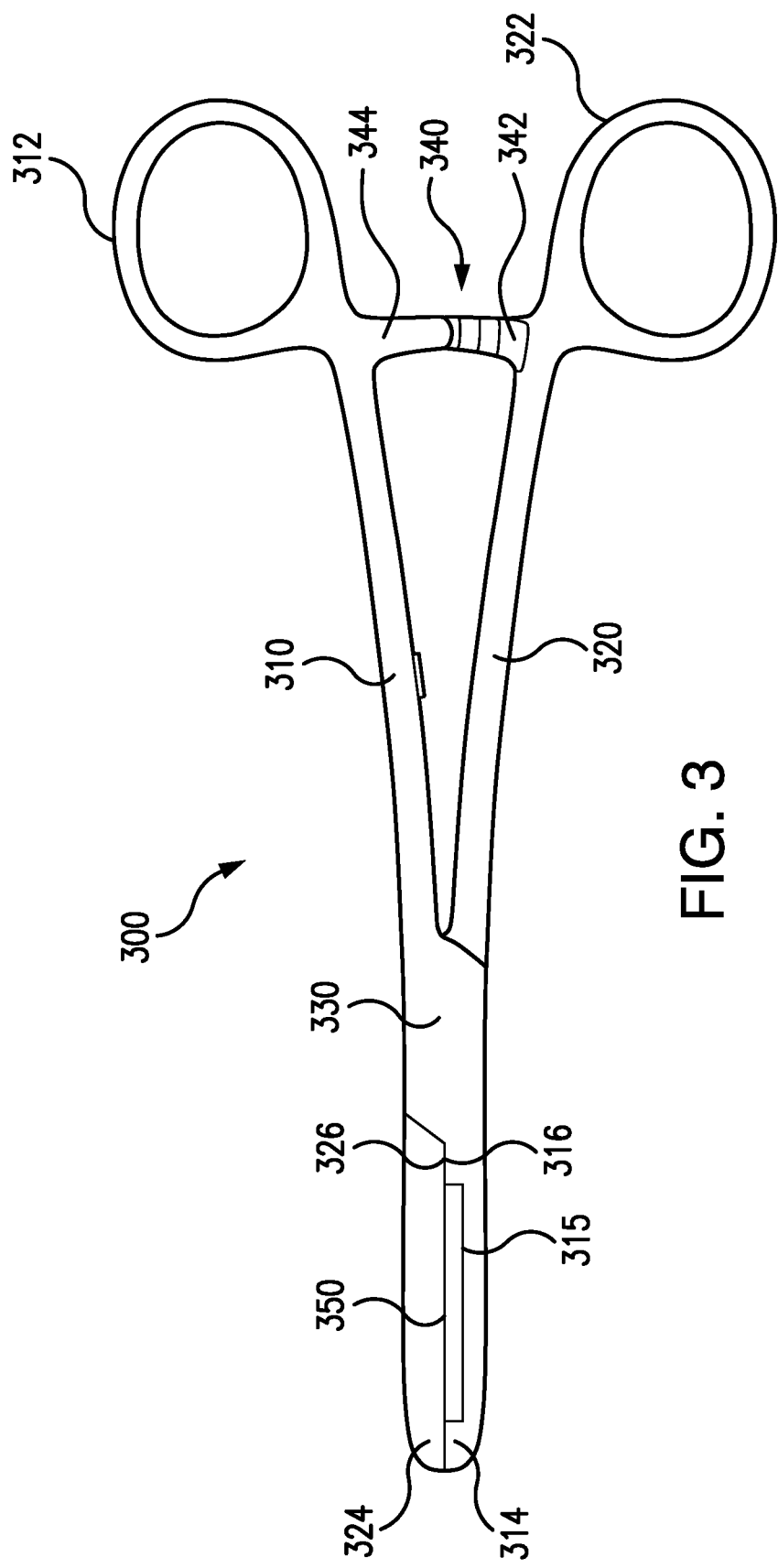
FIG. 3 is a schematic view illustrating a non-limiting example of a removal tool embodying aspects of the present invention.

FIG. 3 illustrates a schematic view of an exemplary removal tool 300 for locating and retrieving the implantable device 100 from the tissue 150 of a host. In some embodiments, as shown in FIG. 3, the removal tool 300 includes a first lever member 310 and a second lever member 320 that are pivotably connected at a joint 330. In some embodiments, the first lever member 310 includes a first handle 312 disposed at a first end thereof and a first jaw member 314 disposed at a second end thereof. In some embodiments, the second lever member 320 includes a second handle 322 disposed at a first end thereof and a second jaw member 314 disposed at a second end thereof. In some non-limiting embodiments, one or more of the first and second handles 312, 314 may include an annular shape.

In some embodiments, the joint 330 may be configured to allow the second ends of the first and second lever members 310, 320 to move correspondingly between a closed position in which the first jaw member 314 abuts against the second jaw member 324 and an open position in which the first jaw member 314 is spatially separated from the second jaw member 324. In some embodiments, the joint 330 may be a hinge, in which one of the first and second lever members 310, 320 includes a socket (not shown) and the other one of the first and second lever members 310, 320 includes a pin (not shown) rotatably received in the socket. In some embodiments, the joint 330 may be disposed proximate to the first and second jaw members 314, 324 and spatially separated from the first and second handles 312, 322.

In some embodiments, the first and second jaw members 314, 324 may comprise opposing engagement surfaces 316, 326 such that the engagement surface 316 of the first lever member 310 abuts against the engagement surface 326 of the second lever member 320 when the first and second jaw members 314, 324 are set at the closed position. In some embodiments, the engagement surfaces 316, 326 may include serrations (not shown) to promote gripping of an object disposed between the first and second jaw members 314, 324.

In some embodiments, the removal tool 300 may include a locking mechanism 340 for locking the first and second jaw member 314, 324 in the closed position, and the first and second jaw members 314, 324 may apply a predetermined amount of pressure against each other in the closed position. In some embodiments, the locking mechanism 340 includes a set of teeth 342 projecting from the second lever member 320 and a hook 344 projecting from the first lever member 310 and configured to be removably coupled to the one of teeth 342 to lock first and second jaw members 314, 324 in the closed position.

In some embodiments, as shown in FIG. 3, the first jaw member 314 may include a magnet 350 that is configured to magnetically attract and couple to the implantable device 100 so that the magnet 350 attracts/guides the implantable device 100 subcutaneously implanted in the tissue of the host to the removal tool 300. In some embodiments, the magnet 350 may comprise one or more ferromagnetic materials (e.g., iron, nickel, and/or cobalt). In some embodiments, the magnet 350 may be configured to apply, for example and without limitation, 1 to 5 pounds of magnetic force, and this pounds of magnetic force range should be understood as describing all pounds of magnetic force (including all decimal and fractional pounds of force) and sub-ranges (e.g., 2 to 4 pounds of magnetic force) within this range. In some embodiments, the magnet 350 may be configured to apply, for example and without limitation, a magnetic flux density of 0.3 T to 0.7 T, and this magnetic flux density range should be understood as describing all magnetic flux densities (including all decimal and fractional magnetic flux densities) and sub-ranges within this range (e.g., 0.5 T and the sub-ranges of 0.4 T to 0.6 T, 0.45 T to 0.55 T, 0.48 T to 0.52 T, and 0.49 T to 0.51 T). In some non-limiting embodiments, the magnet 350 may be configured to magnetically attract to the magnetic core 124 of the inductor 120 disposed in the housing 102 of the implantable device 100. In some embodiments, the magnet 350 may be in shape of a cylinder (e.g., disc), rectangular prism, or any other suitable shape. In some embodiments, as shown in FIG. 3, the first jaw member 314 may include recess 315 corresponding to the shape of the disc magnet 350, such that the disc magnet 350 is received in the recess 315. In some embodiments, the second jaw member 324 may additionally or alternatively include a magnet configured to magnetically attract/guide the implantable device 100 to the removal tool 300. In these embodiments, the second jaw member 324 may include a recess to receive the magnet for the second jaw member 324.

Figure 4:
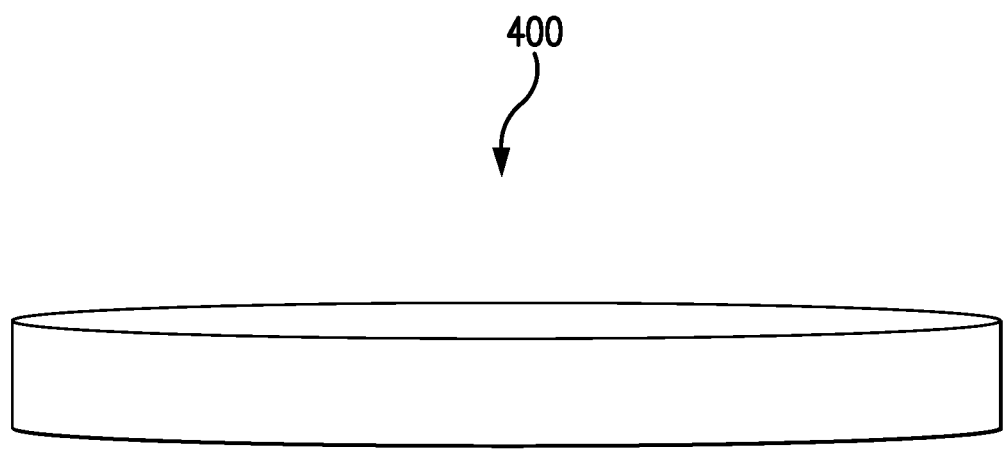
FIG. 4 is a perspective view illustrating a non-limiting example of a disc magnet embodying aspects of the present invention.

FIG. 4 illustrates a perspective view of an exemplary removal tool 400 for locating and retrieving the implantable device 100 from the tissue 150 of a host. In some embodiments, the removal tool 400 may include a magnet. In some embodiments, the magnet may be comprised of a ferromagnetic material (e.g., iron, nickel, and cobalt). In some embodiments, the magnet may be configured to apply, for example and without limitation, 1 to 5 pounds of magnetic force, and this pounds of magnetic force range should be understood as describing all pounds of magnetic force range (including all decimal and fractional pounds of force) and sub-ranges (e.g., 2 to 4 pounds of magnetic force) within this range. In some embodiments, the magnet may be configured to apply, for example and without limitation, a magnetic flux density of 0.3 T to 0.7 T, and this magnetic flux density range should be understood as describing all magnetic flux densities (including all decimal and fractional magnetic flux densities) and sub-ranges within this range (e.g., 0.5 T and the sub-ranges of 0.4 T to 0.6 T, 0.45 T to 0.55 T, 0.48 T to 0.52 T, and 0.49 T to 0.51 T). In some embodiments, the magnet may be configured to magnetically attract to the magnetic core 124 of the inductor 120 disposed in the housing 102 of the implantable device 100. In some embodiments, as shown in FIG. 4, the removal tool 400 may be a disc magnet.

In some embodiments, a process of using the removal tool 400 to remove an implantable device 100 implanted subcutaneously in a tissue pocket 152 below a skin surface 154 of a host may include one or more of the following steps: (a) creating an incision in the skin surface 154; (b) placing the removal tool 400 on the skin surface 154 above the implantable device 100; (c) moving the removal tool 400 toward the incision; and (d) moving the removal tool 400 past the incision. In some embodiments, a magnet of the removal tool 400 placed on the skin surface 154 above the implantable device 100 may attract the implantable device 100. In some embodiments, the attraction of the implantable device to the magnet of the removal tool 400 may not strong enough to break the skin surface. In some embodiments, movement of the removal tool 400 toward the incision may move the implantable device 100 toward the incision. In some embodiments, movement of the removal tool 400 past the incision may move the implantable device 100 out of the tissue pocket 152 and through the incision.

Figure 5:
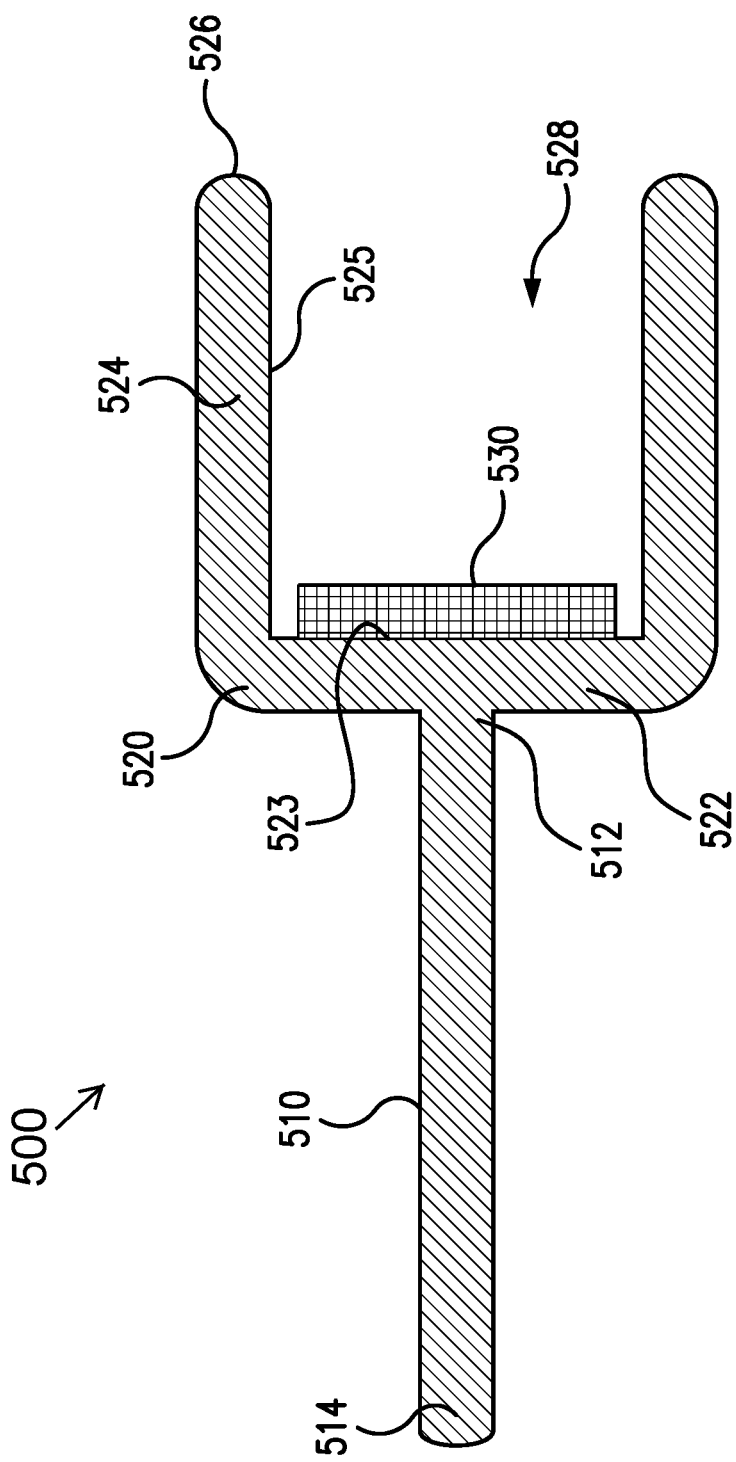
FIG. 5 is a schematic view illustrating a non-limiting example of a removal tool embodying aspects of the present invention.

FIG. 5 illustrates a schematic cross-sectional view of an exemplary removal tool 500 for locating and retrieving the implantable device 100 from the tissue 150 of a host. In some embodiments, the removal tool 500 may include a rod 510 and a cup 520 disposed at a distal end 512 of the rod 510. In some non-limiting embodiments, the cup 520 may be integrally formed with the rod 510 such that the rod 510 and the cup 520 are comprised of a single piece of material. In some alternative embodiments, the cup 520 may be removably coupled to the rod 510. In some embodiments, the rod 510 may include a handle at a proximal end 514 thereof so that a user may grip the rod 510 and orient the cup 520 toward the implantable device 100.

In some embodiments, as shown in FIG. 5, the cup 520 may comprise a base 522, a sidewall 524 projecting from the base 522 (e.g., from an edge of the base 522), and a bore 528 extending from a tip 526 of the sidewall 524 to a face 523 of the base 522. In some embodiments, the cup 520 may comprise an interior surface 525 extending from the tip 526 of the sidewall 524 to the face 523 of the base 522. In some embodiments, the size and shape of the cup 520 may be configured to receive and hold the implantable device 100 within the bore 528.

In some embodiments, as shown in FIG. 5, the removal tool 500 may comprise a magnet 530 in the cup 520. In some non-limiting embodiments, the magnet 530 may be disposed at the face 523 of the base 522. In some embodiments, the magnet 530 is configured to magnetically attract and couple to the implantable device 100 so that the magnet 530 guides the removal tool 500 to the implantable device 100 subcutaneously implanted in the tissue of the host. In some embodiments, the magnet 530 may have a shape suitable for the shape of the cup 520. For example, in embodiments where the cup 520 has a cylindrical shape, the magnet 530 may be a disc magnet. For another example, in embodiments where the cup 520 has a rectangular prism shape, the magnet 530 may have the shape of a rectangular prism. In some embodiments, the magnet 530 may be comprised of a ferromagnetic material (e.g., iron, nickel, and cobalt). In some embodiments, the magnet 530 may be configured to apply, for example and without limitation, 1 to 5 pounds of magnetic force, and this pounds of magnetic force range should be understood as describing all pounds of magnetic force range (including all decimal and fractional pounds of force) and sub-ranges (2 to 4 pounds of magnetic force) within this range. In some embodiments, the magnet 530 may be configured to apply, for example and without limitation, a magnetic flux density of 0.3 T to 0.7 T, and this magnetic flux density range should be understood as describing all magnetic flux densities (including all decimal and fractional magnetic flux densities) and sub-ranges within this range (e.g., 0.5 T and the sub-ranges of 0.4 T to 0.6 T, 0.45 T to 0.55 T, 0.48 T to 0.52 T, and 0.49 T to 0.51 T). In some embodiments, the magnet 530 may be configured to magnetically attract to the ferrite core 124 of the inductor 120 disposed in the housing 102 of the implantable device 100. In some alternative embodiments, the removal tool 500 may comprise a set of magnets (not shown) disposed at the face 523 of the base 522 and configured to magnetically attract and couple to the implantable device 100.

Figure 6:
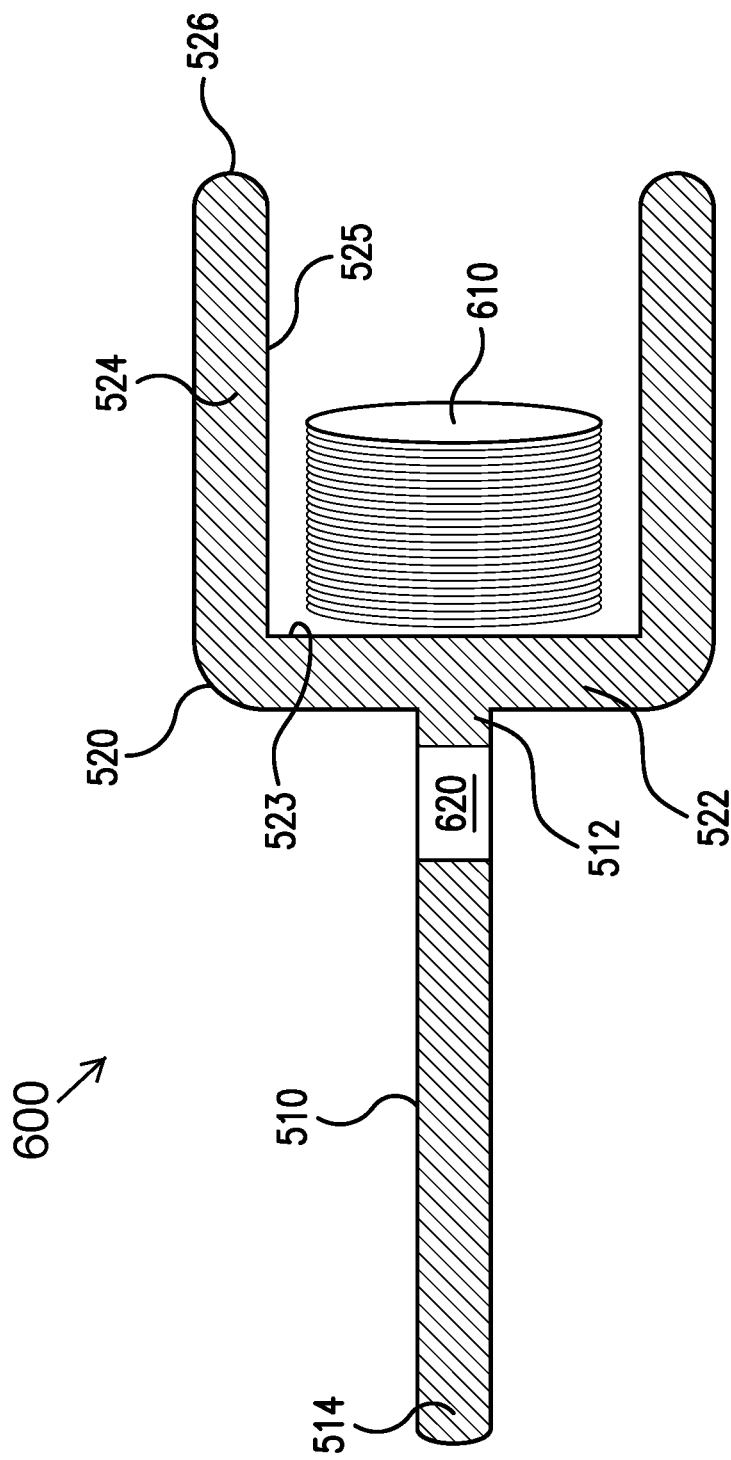
FIG. 6 is a schematic view illustrating a non-limiting example of a removal tool embodying aspects of the present invention.

FIG. 6 illustrates a schematic cross-sectional view of an exemplary removal tool 600 for locating and retrieving the implantable device 100 from the tissue 150 of a host. In some embodiments, the removal tool 600 comprises a rod 510 and a cup 520, which may be the same rod 510 and cup 520 as in the embodiment of the removal tool 500 shown in FIG. 5. In some embodiments, the removal tool 600 may comprise a coil 610 disposed or integrated within the cup 520 and coupled to the face 523 of the base 522. In some embodiments, the removal tool 600 may include circuitry 620. In some non-limiting embodiments, as shown in FIG. 6, the circuitry 620 may be disposed within the rod 510. However, this is not required, and, in some alternative embodiments, the circuitry 620 may be disposed elsewhere (e.g., on the rod 514, in the cup 520, on an outer surface of the cup 520, on interior surface 525 of the cup 520, and/or on the face 523 of the base 522 of the cup 520). In some embodiments, the circuitry 620 may be configured to generate and apply a current to the coil 610, such that the coil 610 generates an electromagnetic field that attracts the coil 610 to the implantable device 100. In various embodiments, the circuitry 620 may comprise any arrangement of electronic components, such as one or more of a power source (e.g., battery), resistors, inductors, capacitors, diodes, ASIC, etc., to generate and apply a current to the coil 610 such that the coil 610 generates the electromagnetic field. In some embodiments, the electromagnetic field may apply, for example and without limitation, 1 to 5 pounds of magnetic force, and this pounds of magnetic force range should be understood as describing all pounds of magnetic force range (including all decimal and fractional pounds of force) and sub-ranges (e.g., 2 to 4 pounds of magnetic force) within this range.

Figure 11A:
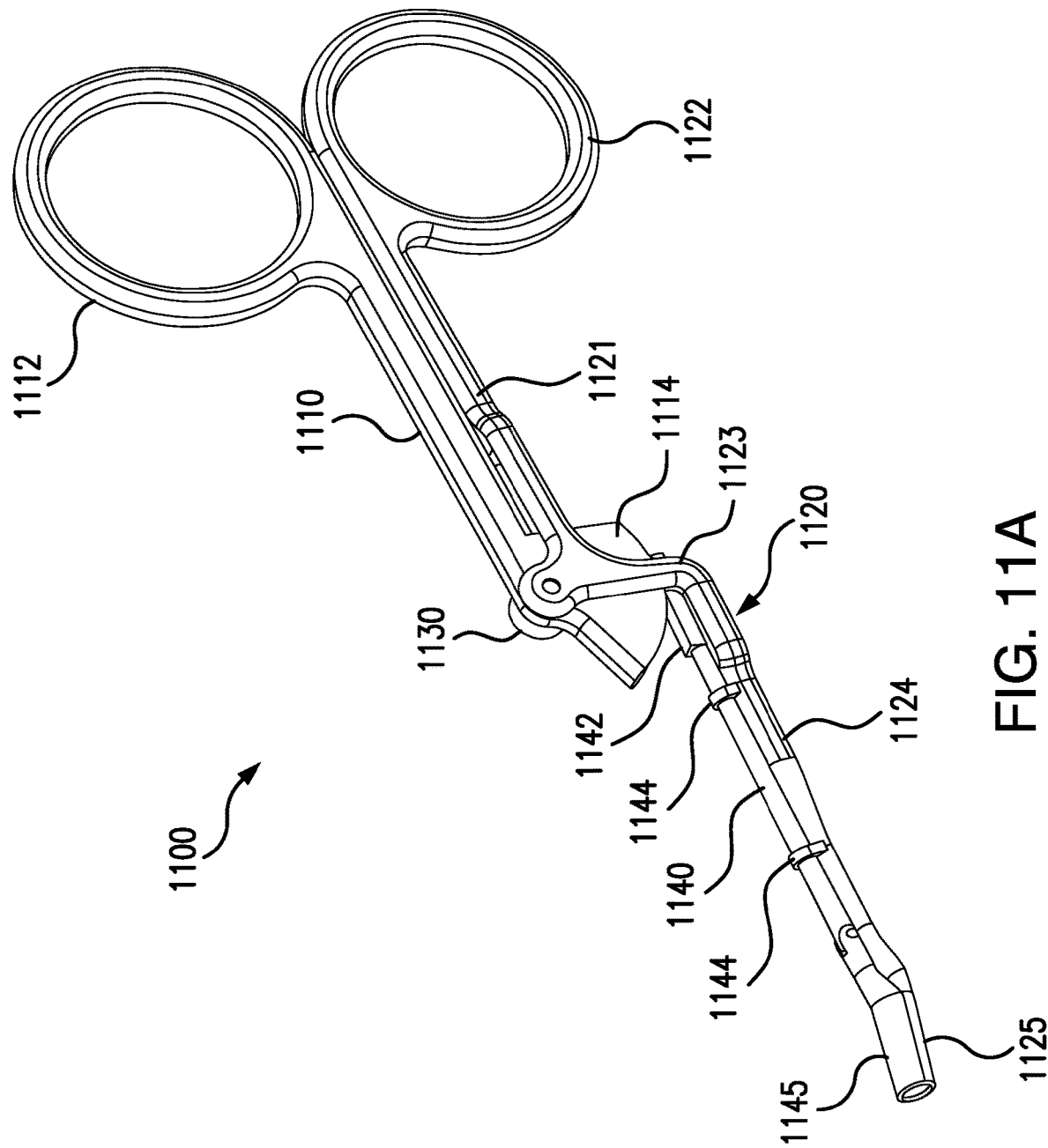
FIGS. 11A and 11B are perspective views of a non-limiting example of a removal tool embodying aspects of the present invention.
Figure 11B:
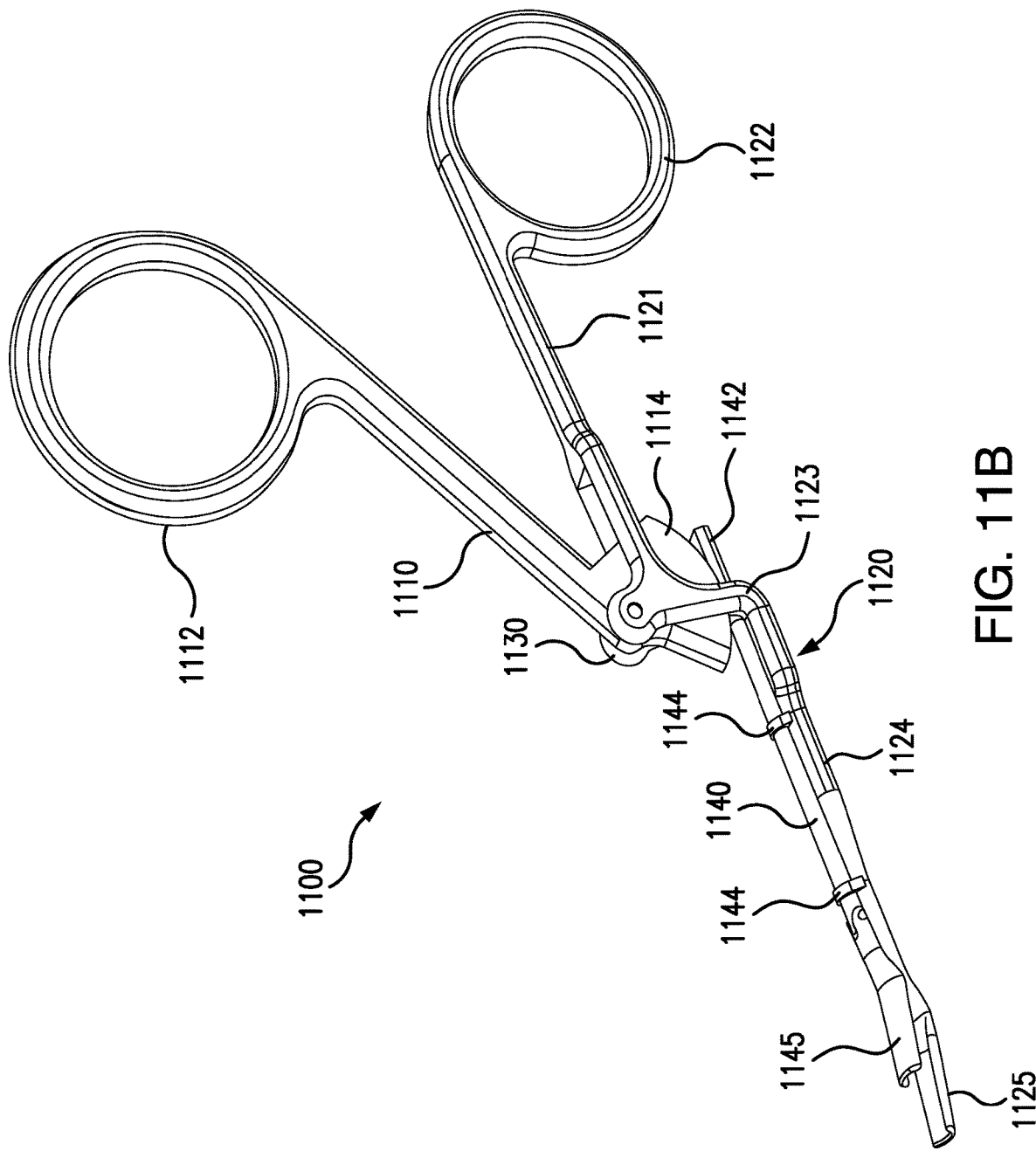

FIGS. 11A and 11B illustrate an exemplary removal tool 1100 for locating and retrieving the implantable device 100 from the tissue 150 of a host. In some embodiments, as shown in FIGS. 11A and 11B, the removal tool 1100 may include a first lever member 1110 and a second lever member 1120 that are pivotably connected at a joint 1130. In some embodiments, the first lever member 1110 may include a first handle 1112 disposed at a first end thereof and an actuator 1114 disposed at a second end thereof. In some embodiments, the second lever member 1120 may include a second handle 1122 disposed at a first end of the second lever member 1120, an upper portion 1121 between the second handle 1122 and the joint 1130, a first jaw member 1125 disposed at a second end of the second lever member 1120, and a lower portion 1124 between the joint 1130 and the first jaw member 1125. In some embodiments, the lower portion 1124 of the second lever member 1120 may include a curved portion 1123 near the joint 1130. In some embodiments, one or more of the first and second handles 1112 and 1122 may include an annular shape.

In some embodiments, the removal tool 1100 may include a rod 1140 having a contact member 1142 at a first end of the rod 1140 and a second jaw member 1145 at a second end of the rod 1140. In some embodiments, the rod 1140 may be parallel to the lower portion 1124 of the second lever member 1120. In some embodiments, the lower portion 1124 of the second lever member 1120 may include one or more holders 1144 (e.g., rings). In some embodiments, the rod 1140 may pass through the one or more holders 1144. In some embodiments, the one or more holders 1144 may hold the rod 1140 in a position that is parallel and adjacent to the lower portion 1124 of the second lever member 1120 while allowing the rod 1140 to slide forward and backwards.

In some embodiments, the actuator 1114 of the first lever member 1110 may be in contact with the with contact member 1142 of the rod 1140. In some embodiments, movement of the actuator 1114 may cause movement of the rod 1140. In some embodiments, one or more of the actuator 1114 and the contact member 1142 may include teeth, grooves, projections, and/or other structures such that movement of the actuator 1114 causes movement of the rod 1140. In some embodiments, movement of the first and second handles 1112 and 1122 from a closed position, as shown in FIG. 11A, to an open position, as shown in FIG. 11B, may cause movement (e.g., rotation) of the actuator 1114 of the first lever member 1110, which causes movement of the rod 1140 (and of the second jaw member 1145) from an extended position, as shown in FIG. 11A, to a retracted position, as shown in FIG. 11B. In some embodiments, movement of the first and second handles 1112 and 1122 from the open position, as shown in FIG. 11B, to the closed position, as shown in FIG. 11A, may cause movement (e.g., rotation) of the actuator 1114 of the first lever member 1110, which causes movement of the rod 1140 (and of the second jaw member 1145) from the retracted position, as shown in FIG. 11B, to the extended position, as shown in FIG. 11A.

In some embodiments, the first and second jaw members 1125 and 1145 may have a shape that matches the shape of the implantable device 100. For example, if the implantable device 100 has a cylindrical shape as shown in FIG. 1, the first and second jaw members 1125 and 1145 may be rounded such that the first and second jaw members 1125 and 1145 together form a hollow cylindrical shape when the rod 1140 (and therefore the second jaw member 1145) is at the extended position. In some embodiments, the first and second jaw members 1125 and 1145 may have a shape that is customized to match the shape of the implantable device 100. In some embodiments, one or more of the first and second jaw members 1125 and 1145 may have a sharp end. In some embodiments, the sharp end of the first and/or second jaw members 1125 and 1145 may allow the first and/or second jaw members 1125 and 1145 to dissect through in-grown tissue.

In some embodiments, in use, after an incision is created in the skin surface 154, with the second jaw member 1145 in the retracted position (see FIG. 11B), the first jaw member 1125 may pass through the incision and be correctly positioned below the implantable device 100. In some embodiments, a sharp end of the first jaw member 1125 may dissect through in-grown tissue on its way to being positioned below the implantable device 100. In some embodiments, the first and second handles 1112 and 1122 may be moved from the open position (see FIG. 11B) to the closed position (see FIG. 11A), which may move the second jaw member 1145 from the retracted position (see FIG. 11B) to the extended position (see FIG. 11A) to accurately position second jaw member 1145 above the implantable device 100. In some embodiments, a sharp end of the second jaw member 1145 may dissect through in-grown tissue on its way to being positioned above the implantable device 100.

In some embodiments, the removal tool 1100 shown in FIGS. 11A and 11B may provide one or more advantages relative to standard clamps with respect to the extraction of an implantable device. Standard clamps are not ideal for extracting medical devices that have been implanted for extended period of time. The primary drawbacks of standard clamps may include one or more of (i) incompatibility of the standard clamp tip to the exact shape of the implantable device, (ii) the need for a large entry incision because the standard clamp needs to be inserted in an open position (with the jaw member separated from one another) to help grab the sensor, and (iii) tissue attached to implantable device being pulled out with implantable device (instead of being dissected). Each of the drawbacks listed above lead to excessive trauma and bleeding. In contrast to standard clamps, the removal tool 1100 may provide one or more of the following advantages: (i) the shape of the first and second jaw members 1125 and 1145 matching the shape of the implantable device, (ii) a relatively small entry incision is required the first jaw member 1125 is inserted with the second jaw member 1145 in the retracted position (instead of a position in which the second jaw member is separated from the first jaw member), and (iii) the sharps ends of the first and second jaw members 1125 and 1145 dissect tissue that has grown into and/or attached to implantable device 100 (instead of pulling out the implantable device 100 when extracting the device 100).

Figure 7:
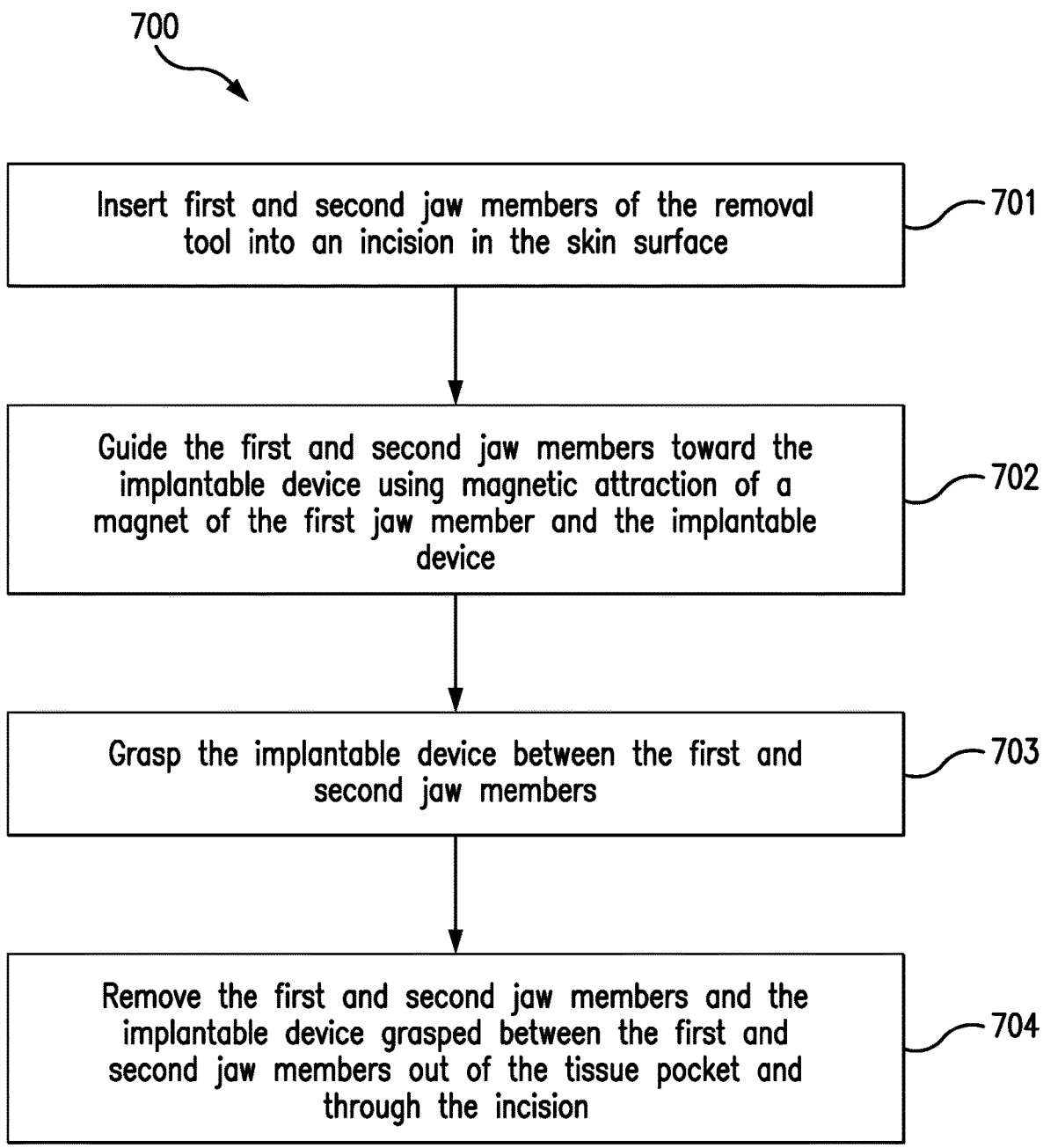
FIG. 7 illustrates a method of removing an implantable device by using the removal tool shown in FIG. 3 embodying aspects of the present invention.

FIG. 7 illustrates a method 700 of removing an implantable device subcutaneously implanted in a tissue pocket below a skin surface of a host embodying aspects of the present disclosure. In some embodiments, the removal tool 300 described above with reference to FIG. 3 may be used to remove the implantable device according to the method described in FIG. 7.

In some embodiments, the method 700 may include a preliminary step of creating an incision in a skin surface 154. In some embodiments, the incision may be, for example and without limitation, 6-8 mm wide and 4-6 mm deep. However, these dimensions are not required, and some alternative embodiments may use different dimensions.

In some embodiments, the method 700 may include a step 701 of inserting the first jaw member 314 of a first lever member 310 of the removal tool 300 and the second jaw member 324 of the second lever member 320 of the removal tool 300 into an incision in the skin surface 154.

In some embodiments, the method 700 may include a step 702 of guiding the first jaw member 314 and the second jaw member 324 toward the implantable device 100 by using magnetic attraction of the magnet 350 in the first jaw member 314 and the implantable device 100. In some embodiments, the step 702 of guiding the first and second jaw members 314, 324 toward the implantable device 100 may include using magnetic attraction of the magnet 350 of the first jaw member 314 and the magnetic core 124 of the implantable device 100.

In some embodiments, the method 700 may include a step 703 of grasping the implantable device 100 between the first and second jaw members 114, 124. In some embodiments, step 704 may further include using magnetic force generated by the magnet 350 to dislodge or pull the implantable device 100 out of the tissue pocket 152. In some embodiments, during step 704, the first and second lever members 310, 320 pivot about the joint 330 to move the first and second jaw members 314, 324 toward a closed position, such that the implantable device 100 is held against opposing engagement surfaces 316, 326 of the first and second jaw members 314, 324. In some embodiments, the grasped implantable device 100 may be coupled magnetically to the first jaw member 314.

In some embodiments, the method 700 may include a step 704 of removing the first and second jaw members 314, 324 and the implantable device 100 grasped between the first and second jaw members 314, 324 out of the tissue pocket 152 and through the incision.

Figure 8:
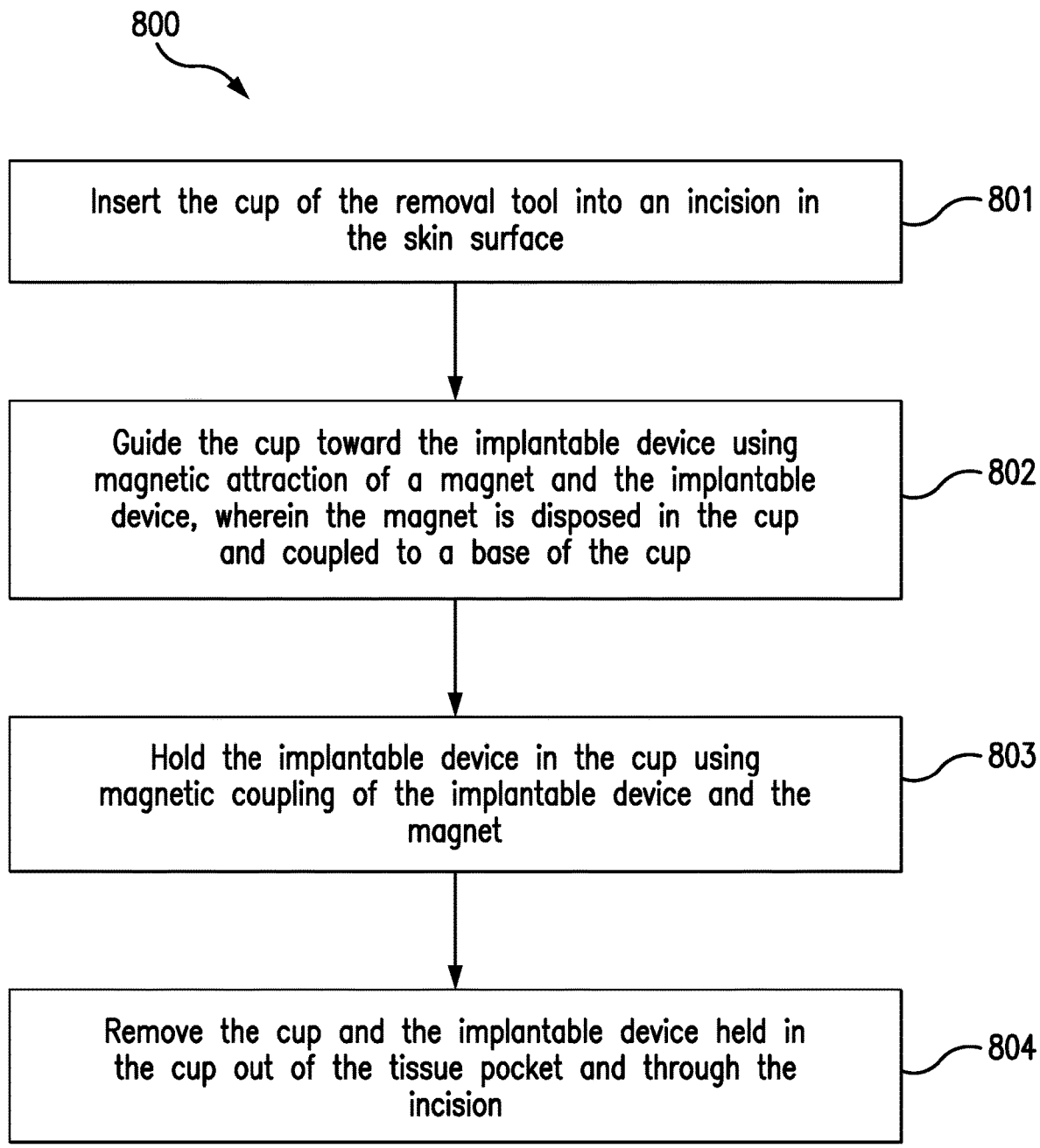
FIG. 8 illustrates a method of removing an implantable device by using the removal tool shown in FIG. 5 embodying aspects of the present invention.

FIG. 8 illustrates a method 800 of for removing an implantable device subcutaneously implanted in a tissue pocket below a skin surface of a host embodying aspects of the present disclosure. In some embodiments, the removal tool 500 described above with reference to FIG. 5 may be used to remove the implantable device according to the method described in FIG. 8.

In some embodiments, the method 800 may include a preliminary step of creating an incision in a skin surface 154. In some embodiments, the incision may be, for example and without limitation, 6-8 mm wide and 4-6 mm deep. However, these dimensions are not required, and some alternative embodiments may use different dimensions.

In some embodiments, the method may include a step 801 of inserting the cup 520 disposed at the distal end of the rod 510 of the removal tool 600 into the incision in the skin surface 154.

In some embodiments, the method may include a step 802 of guiding the cup 520 toward the implantable device 100 using magnetic attraction of the magnet 530 and the implantable device 100, in which the magnet 530 is disposed in the cup 520 and coupled to the base 522 of the cup 520. In some embodiments, the step 802 of guiding the cup 520 toward the implantable device 100 may use magnetic attraction of the magnet 530 and the magnetic core 124 of the implantable device 100. In some embodiments, the step 802 of guiding the cup 520 may result in the implantable device 100 being received in the cup 520.

In some embodiments, the method may include a step 803 of holding the implantable device 100 in the cup 520 using magnetic coupling of the implantable device 100 and the magnet 530. In some embodiments, step 804 further includes using magnetic force generated by the magnet 530 to dislodge or pull the implantable device 100 out of the tissue pocket 152.

In some embodiments, the method may include a step 804 of removing the cup 520 and the implantable device 100 held in the cup 520 out of the tissue pocket 152 and through the incision.

Figure 9:
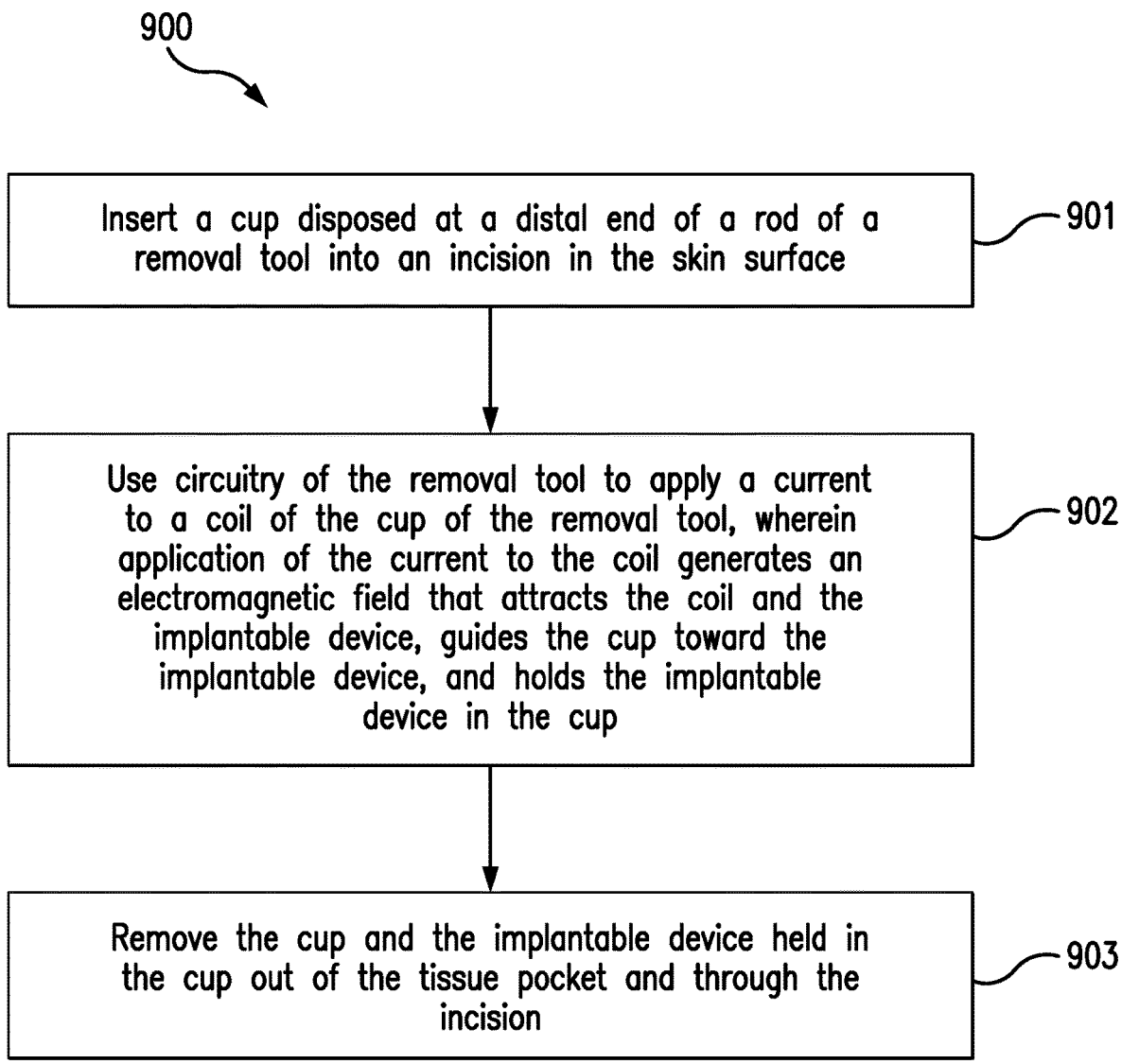
FIG. 9 illustrates a method of removing an implantable device using the removal tool shown in FIG. 6 embodying aspects of the present invention.

FIG. 9 illustrates a method 900 of for removing an implantable device subcutaneously implanted in a tissue pocket below a skin surface of a host embodying aspects of the present disclosure. In some embodiments, the removal tool 600 described above with reference to FIG. 6 may be used to remove the implantable device according to the method described in FIG. 9.

In some embodiments, the method 800 may include a preliminary step of creating an incision in a skin surface 154. In some embodiments, the incision may be, for example and without limitation, 6-8 mm wide and 4-6 mm deep. However, these dimensions are not required, and some alternative embodiments may use different dimensions.

In some embodiments, the method may include a step 901 of inserting the cup 520 disposed at the distal end of the rod 510 of the removal tool 600 into the incision in the skin surface 154. In some embodiments, the step of 901 of inserting the cup 520 may include using the handle 514 to insert the cup 520 into the incision.

In some embodiments, the method may include a step 902 of using the circuitry 620 of the removal tool 600 to apply a current to the coil 610 of the cup 520 of the removal tool 600, wherein application of the current to the coil 610 generates an electromagnetic field that attracts the coil 610 and the implantable device 100, guides the cup 520 toward the implantable device 100, and holds the implantable device 100 in the cup 520. In some embodiments, the step 902 of using the circuitry 620 to apply the current may result in the implantable device 100 being received in the cup 520.

In some embodiments, the method may include a step 903 of removing the cup 520 and the implantable device 100 held in the cup 520 out of the tissue pocket 152 and through the incision. In some embodiments, the step of 903 of removing the cup 520 and the implantable device 100 held in the cup 520 may include using the handle 514.

Figure 10:
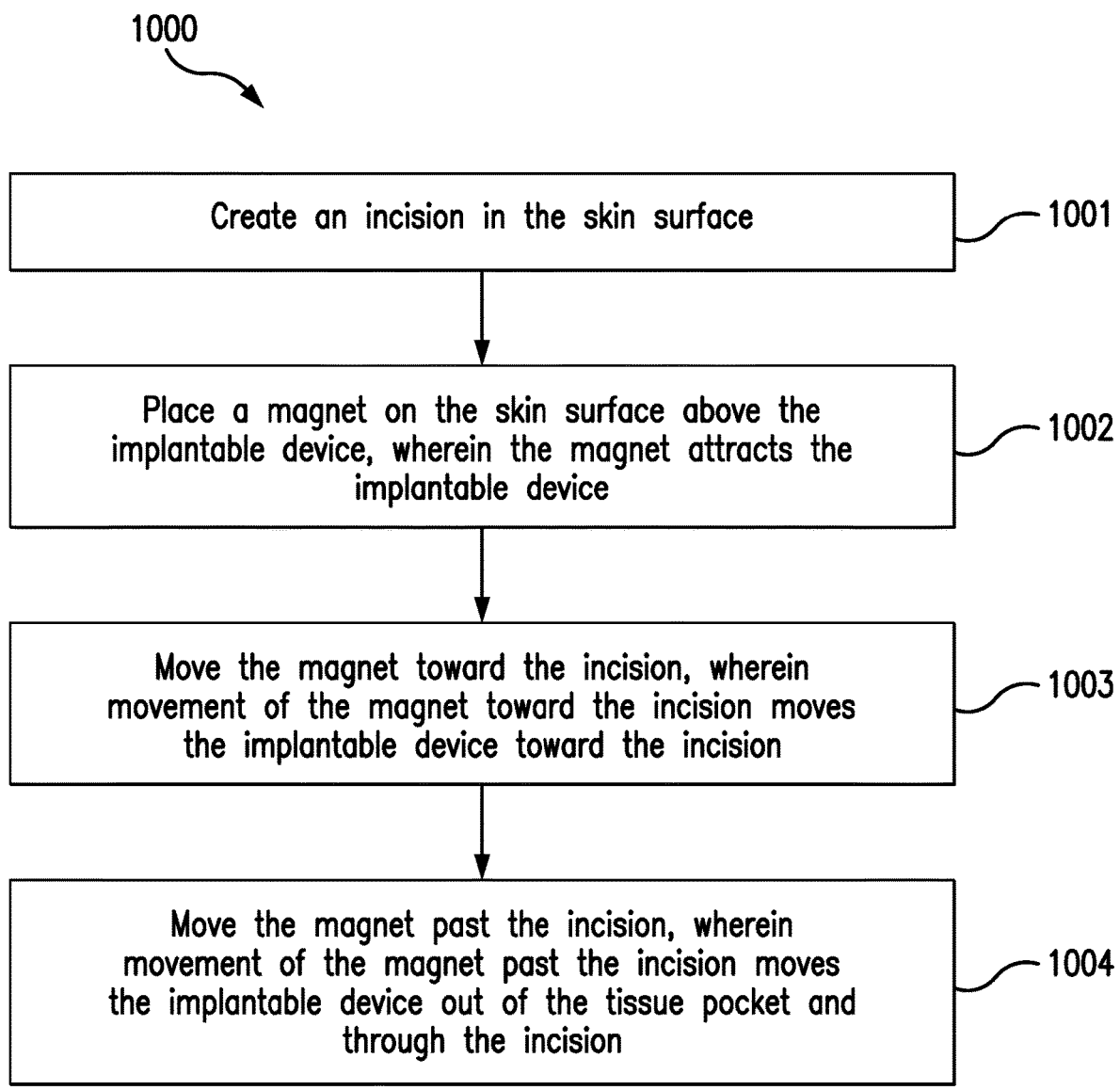
FIG. 10 illustrates a method of removing an implantable device using the removal tool shown in FIG. 4 embodying aspects of the present disclosure.

FIG. 10 illustrates a method 1000 of for removing an implantable device subcutaneously implanted in a tissue pocket below a skin surface of a host embodying aspects of the present disclosure. In some embodiments, the removal tool 400 described above with reference to FIG. 4 may be used to remove the implantable device according to the method described in FIG. 10.

In some embodiments, the method 1000 may include a step 1001 of creating an incision in the skin surface.

In some embodiments, the method 1000 may include a step 1002 of placing the magnet on the skin surface above the implantable device 100, wherein the magnet attracts the implantable device 100.

In some embodiments, the method 1000 may include a step 1003 of moving the magnet toward the incision, wherein movement of the magnet toward the incision moves the implantable device 100 toward the incision.

In some embodiments, the method may include a step 1004 of moving the magnet past the incision, wherein movement of the magnet past the incision moves the implantable device 100 out of the tissue pocket and through the incision.

Figure 12:
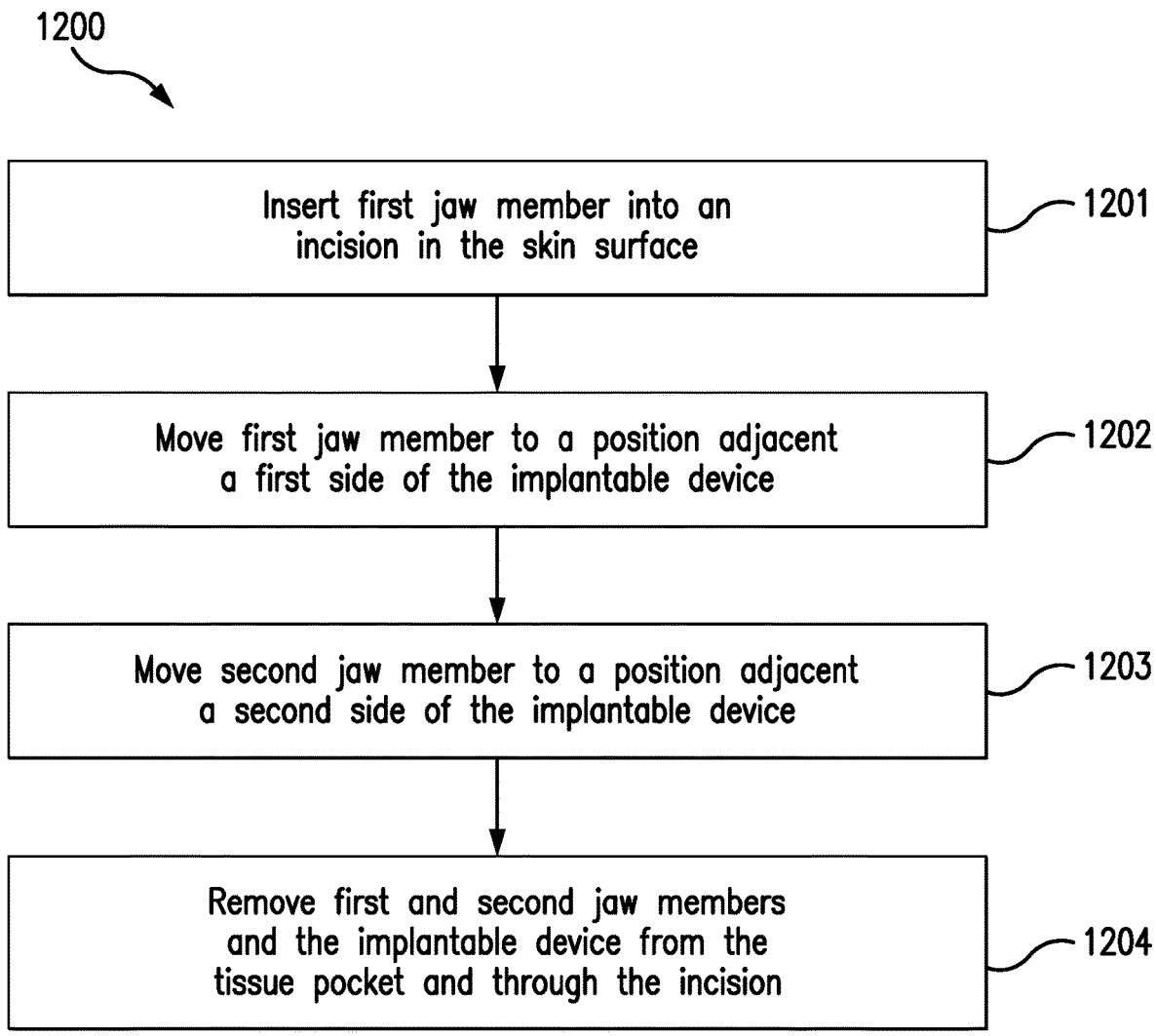
FIG. 12 illustrates a method for removing an implantable device using the removal tool shown in FIGS. 11A and 11B embodying aspects of the present invention.

FIG. 12 illustrates a method 1200 of removing an implantable device 100 subcutaneously implanted in a tissue pocket 152 below a skin surface 154 of a host embodying aspects of the present disclosure. In some embodiments, the removal tool 1100 described above with reference to FIGS. 11A and 11B may be used to remove the implantable device according to the method described in FIG. 12.

In some embodiments, the method 1200 may include a preliminary step of creating an incision in a skin surface 154. In some embodiments, the incision may be, for example and without limitation, 6-8 mm wide and 4-6 mm deep. However, these dimensions are not required, and some alternative embodiments may use different dimensions.

In some embodiments, the method 1200 may include a step 1201 of inserting the first jaw member 1125 of the second lever member 1120 of the removal tool 1100 into an incision in the skin surface 154. In some embodiments, the first jaw member 1125 of the second lever member 1120 may be inserted into the incision with the second jaw member 1145 in the retracted position and the first and second handles 1112 and 1122 in the open position as shown in FIG. 11B.

In some embodiments, the method 1200 may include a step 1202 of moving the first jaw member 1125 to a position adjacent to a first side of the implantable device 100 (e.g., a position below the implantable device 100). In some embodiments, a sharp end of the first jaw member 1125 may dissect tissue attached to the first side (e.g., a lower half) of the implantable device 100 on its way to is position below the implantable device.

In some embodiments, the method 1200 may include a step 1203 moving the second jaw member 1145 of the rod 1140 of the removal tool 1100 to a position adjacent to a second side of the implantable device 100 (e.g., a position above the implantable device 100). In some embodiments, the first side of the implantable device 100 may be opposite the second side of the implantable device 100. In some embodiments, moving the second jaw member 1145 to the position adjacent to the second side of the implantable device 100 may include moving the second jaw member 1145 from the retracted position (see FIG. 11B) to the extended position (see FIG. 11A). In some embodiments, moving the first and second handles 1112 and 1122 from the open position (see FIG. 11B) to the closed position (see FIG. 11A) may cause the second jaw member 1145 to move from the retracted position to the extended position. In some embodiments, when the first and second handles 1112 and 1122 are moved from the open position to the closed position, the actuator 1114 of the first lever member 1110, which is in contact with the contact portion 1142 of the rod 1140, may move (e.g., rotate) and cause the rod 1140 to move forward, which causes the second jaw member 1145 at an end of the rod 1140 to move forward to the extended position. In some embodiments, a sharp end of the second jaw member 1145 may dissect tissue attached to the second side (e.g., an upper half) of the implantable device 100 on its way to is position above the implantable device. In some embodiments, with the second jaw member 1145 moved to the position above the implantable device 100, the first and second jaw members 1125 and 1145 may grasp the implantable device 100.

In some embodiments, the method 1200 may include a step 1204 of removing the first and second jaw members 1125 and 1145 and the implantable device 100 grasped between the first and second jaw members 1125 and 1145 out of the tissue pocket 152 and through the incision.

Figure 13:
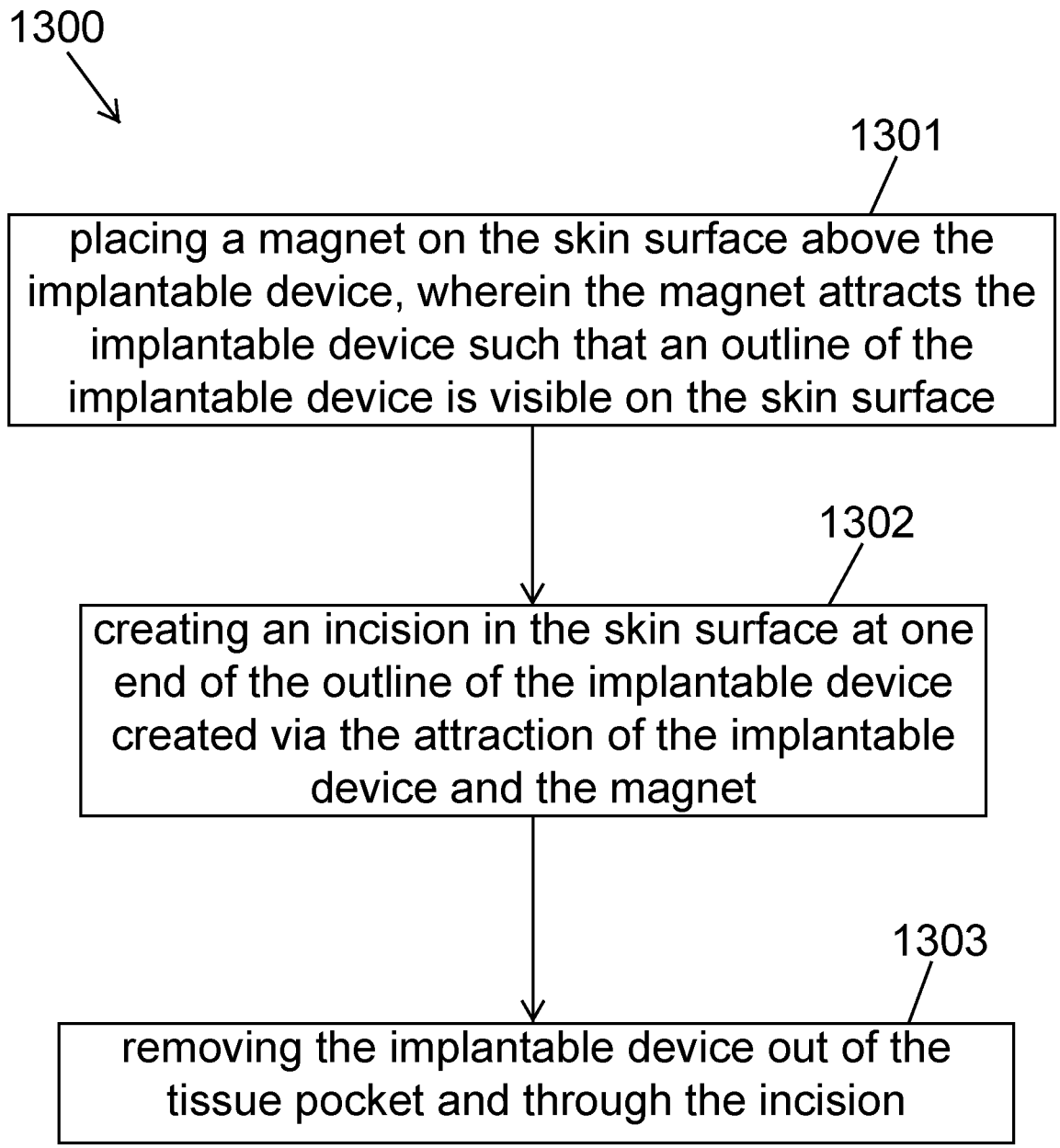
FIG. 13 illustrates a method for removing an implantable device embodying aspects of the present invention.

FIG. 13 illustrates a method 1300 of removing an implantable device 100 subcutaneously implanted in a tissue pocket 152 below a skin surface 154 of a host embodying aspects of the present disclosure.

In some embodiments, the method 1300 may include a step 1301 of placing a magnet on the skin surface 154 above the implantable device 100. In some embodiments, the magnet may be configured to apply, for example and without limitation, 1 to 5 pounds of magnetic force, and this pounds of magnetic force range should be understood as describing all pounds of magnetic force range (including all decimal and fractional pounds of force) and sub-ranges (e.g., 2 to 4 pounds of magnetic force) within this range. In some embodiments, the magnet may be configured to apply, for example and without limitation, a magnetic flux density of 0.3 T to 0.7 T, and this magnetic flux density range should be understood as describing all magnetic flux densities (including all decimal and fractional magnetic flux densities) and sub-ranges within this range (e.g., 0.5 T and the sub-ranges of 0.4 T to 0.6 T, 0.45 T to 0.55 T, 0.48 T to 0.52 T, and 0.49 T to 0.51 T). In some embodiments, the magnet may be configured to magnetically attract to the magnetic core 124 of the inductor 120 disposed in the housing 102 of the implantable device 100. In some embodiments, the magnet may be a disc magnet, such as the disc magnet illustrated in FIG. 4.

In some embodiments, when the magnet attracts the implantable device 100, the tissue between the magnet and the implantable device 100 will be pinched or squeezed between the magnet and the implantable device 100, and an outline of the implantable device 100 may be visible on the skin surface 154. Because the outline of the implantable device 100 may be visible on the skin surface 154 when the magnet is placed on the skin surface 154 above the implantable device 100, the magnet may assist with identifying the location of the implantable device 100 below the skin surface 154. In some embodiments, the method 1300 may include a step 1302 of creating an incision in the skin surface 154 at the outline of the implantable device 100 created via the attraction of the implantable device 100 to the magnet (e.g., at one end of the outline of the implantable device). In some embodiments, using the magnet to identify the location of the implantable device 100 below the skin surface 154 may facilitate creation of the incision at the correct location relative to the implantable device 100. In some embodiments, using the magnet to identify the location of the implantable device 100 below the skin surface 154 may improve the accuracy of the location of the incision in the skin surface.

In some embodiments, the method 1300 may include a step 1303 of removing the implantable device 100 out of the tissue pocket 152 and through the incision. In some embodiments, a removal tool may be used to remove the implantable device 100 in step 1303. In some embodiments, the removal tool may any of the removal tool 300, the removal tool 400, removal tool 500, the removal tool 600, and the removal tool 1100, which are illustrated in FIGS. 3-6 and 11, respectively. However, this is not required, and, in some alternative embodiments, a convention removal tool may be used in step 1303 to remove the implantable device 100 out of the tissue pocket 152 and through the incision. In some embodiments, the step 1303 may include the steps of any of methods 700, 800, 900, 1000, and 1200 (other than an incision creation step). However, this is not required. In some alternative embodiments, the step 1303 may include inserting first and second jaw members of a conventional removal tool into the incision in the skin surface 154, grasping the implantable device 100 between the first and second jaw members, and removing the first and second jaw members and the implantable device grasped between the first and second jaw members out of the tissue pocket 152 and through the incision.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. A method of removing an implantable device implanted subcutaneously in a tissue pocket below a skin surface of a host, the method comprising:
(a) placing a magnet on the skin surface above the implantable device, wherein the magnet attracts the implantable device such that an outline of the implantable device is visible on the skin surface;

(b) while the magnet is on the skin surface above the implantable device and the attraction of the implantable device and the magnet is creating the outline of the implantable device, creating an incision in the skin surface at one end of the outline of the implantable device;

(c) removing the implantable device out of the tissue pocket and through the incision.

2. The method of claim 1, wherein the magnet is configured to apply 2 to 4 pounds of magnetic force.

3. The method of claim 1, wherein the magnet is configured to apply a magnetic flux within the range of 0.45 T to 0.55 T.

4. The method of claim 1, wherein removing the implantable device out of the tissue pocket and through the incision comprises:

(c1) inserting a first jaw member of a removal tool and a second jaw member of the removal tool into the incision in the skin surface;

(c2) grasping the implantable device between the first and second jaw members; and (c3) removing the first and second jaw members and the implantable device grasped between the first and second jaw members out of the tissue pocket and through the incision.

5. The method of claim 1, wherein removing the implantable device out of the tissue pocket and through the incision comprises:

(c1) inserting a first jaw member of a first lever member of a removal tool and a second jaw member of a second lever member of the removal tool into the incision in the skin surface;

(c2) guiding the first jaw member and the second jaw member toward the implantable device using magnetic attraction of a magnet of the first jaw member and the implantable device;

(c3) grasping the implantable device between the first and second jaw members; and (c4) removing the first and second jaw members and the implantable device grasped between the first and second jaw members out of the tissue pocket and through the incision.

6. The method of claim 5, wherein grasping the implantable device comprises pivoting the first and second lever members about a joint to move the first and second jaw members toward a closed position, such that the implantable device is held against opposing engagement surfaces of the first and second jaw members.

7. The method of claim 5, wherein the grasped implantable device is coupled magnetically to the first jaw member.

8. The method of claim 5, wherein guiding the first and second jaw members comprises setting the first and second jaw members in an open position and receiving the implantable device between opposing engagement surfaces of the first and second jaw members.

9. The method of claim 5, wherein guiding the first and second jaw members toward the implantable device uses magnetic attraction of the magnet of the first jaw member and a magnetic core of the implantable device.

10. The method of claim 1, wherein removing the implantable device out of the tissue pocket and through the incision comprises:

(c1) inserting a cup disposed at a distal end of a rod of a removal tool into the incision in the skin surface;

(c2) guiding the cup toward the implantable device using magnetic attraction of a magnet and the implantable device, wherein the magnet is disposed in the cup and coupled to a base of the cup;

(c3) holding the implantable device in the cup using magnetic coupling of the implantable device and the magnet; and (c4) removing the cup and the implantable device held in the cup out of the tissue pocket and through the incision.

11. The method of claim 1, wherein removing the implantable device out of the tissue pocket and through the incision comprises:

(c1) inserting a cup disposed at a distal end of a rod of a removal tool into the incision in the skin surface;

(c2) using circuitry of the removal tool to apply a current to a coil of the cup of the removal tool, wherein application of the current to the coil generates an electromagnetic field that attracts the coil and the implantable device, guides the cup toward the implantable device, and holds the implantable device in the cup; and (c3) removing the cup and the implantable device held in the cup out of the tissue pocket and through the incision.

12. The method of claim 1, wherein removing the implantable device out of the tissue pocket and through the incision comprises:

moving first and second handles of a removal tool from an open position in which the first and second handles are relatively far from each other to a closed position in which the first and second handles are relatively close each other, wherein the first handle is at a first end of a first lever member, an actuator is at a second end of the first lever member, the second handle is at a first end of a second lever member, and a first jaw member is at a second end of the second lever member;

wherein movement of the first and second handles from the open position to the closed position moves a second jaw member from a retracted position to an extended position, the actuator is contact with a contact portion of a rod at a first end of the rod, and the second jaw member is at a second end of the rod.

13. A method of removing an implantable device implanted subcutaneously in a tissue pocket below a skin surface of a host, the method comprising:

placing a magnet on the skin surface above the implantable device, wherein the magnet attracts the implantable device;

moving the magnet toward an incision created in the skin surface, wherein movement of the magnet toward the incision moves the implantable device toward the incision; and moving the magnet past the incision, wherein movement of the magnet past the incision moves the implantable device out of the tissue pocket and through the incision.

14. A removal tool comprising:

a first lever member comprising a first handle at a first end of the first lever member and an actuator at a second end of the first lever member;

a second lever member comprising a second handle at a first end of the second lever member and a first jaw member at a second end of the second lever member; and a rod comprising a contact portion at a first end of the rod and a second jaw member at a second end of the rod;

wherein the actuator of the first lever member is configured to contact the contact portion of the rod;

wherein the first lever member is pivotably coupled to the second lever member at a joint such that the first and second handles are configured to move between an open position in which the first and second handles are relatively far from each other and a closed position in which the first and second handles are relatively close to each other;

wherein movement of the first and second handles from the open position to the closed position is configured to move the second jaw member in a direction of a longitudinal axis of the rod from a retracted position in which the second jaw member is displaced from the first jaw member to an extended position in which the second jaw member is positioned opposite the first jaw member.

15. The removal tool of claim 14, wherein the second lever member further comprises an upper portion between the second handle and the joint and a lower portion between the joint and the first jaw member.

16. The removal tool of claim 15, wherein the lower portion of the second lever member includes a curved portion near the joint.

17. The removal tool of claim 15, wherein the rod is parallel to the lower portion of the second lever member.

18. The removal tool of claim 15, wherein the lower portion of the second lever member includes one or more holders, and the rod passes through the one or more holders.

19. The removal tool of claim 14, wherein movement of the first and second handles between the open and closed positions causes movement of the actuator, and movement of the actuator causes movement of the rod.

20. The removal tool of claim 14, wherein the first and second jaw members have a curved shape.

21. The removal tool of claim 14, wherein the first and second jaw members together form a hollow cylindrical shape when the second jaw member is at the extended position.

22. The removal tool of claim 14, wherein the first and second jaw members each have a shape that matches the shape of an implantable device.

23. The removal tool of claim 14, wherein the first and second jaw members each have sharp end configured to dissect tissue attached to an implantable device.

24. A method of using a removal tool, the method comprising:

moving first and second handles of the removal tool from an open position in which the first and second handles are relatively far from each other to a closed position in which the first and second handles are relatively close each other, wherein the first handle is at a first end of a first lever member, an actuator is at a second end of the first lever member, the second handle is at a first end of a second lever member, a first jaw member is at a second end of the second lever member, and the actuator is contact with a contact portion at a first end of a rod;

wherein movement of the first and second handles from the open position to the closed position moves a second jaw member at a second end of the rod in a direction of a longitudinal axis of the rod from a retracted position in which the second jaw member is displaced from the first jaw member to an extended position in which the second jaw member is positioned opposite the first jaw member.

25. The method of claim 24, wherein movement of the first and second handles from the open to the closed position causes movement of the actuator, and the movement of the actuator causes movement of the rod.

26. A method for removing an implantable device implanted subcutaneously in a tissue pocket below a skin surface of a host, the method comprising:
(a) inserting a first jaw member of the removal tool into an incision in the skin surface;
(b) moving the first jaw member to a position adjacent to a first side of the implantable device, wherein moving the first jaw member to the position adjacent to the first side of the implantable device comprises dissecting tissue attached to the first side of the implantable device;
(c) after moving the first jaw member to the position adjacent to the first side of the implantable device, moving a second jaw member of the removal tool to a position adjacent to a second side of the implantable device, wherein the second side of the implantable device is opposite the first side of the implantable device, moving the second jaw member to the position adjacent to the second side comprises moving first and second handles of the removal tool from an open position in which the first and second handles are relatively far from each other to a closed position in which the first and second handles are relatively close each other, moving the first and second handles from the open position to the closed position causes the second jaw member to move from a retracted position to an extended position, movement of the second jaw member from the retracted position to the extended position dissects tissue attached to the second side of the implantable device, and the first and second jaw members grasp the implantable device when in the positions adjacent to the first and second sides of the implantable device, respectively; and
(d) removing the first and second jaw members and the implantable device grasped between the first and second jaw members out of the tissue pocket and through the incision.

27. The method of claim 26, further comprising creating the incision in a skin surface.

28. The method of claim 26, wherein the position adjacent to the first side of the implantable device is below the implantable device, and the position adjacent to the second side of the implantable device is above the implantable device.

29. The method of claim 26, wherein the first handle is at a first end of a first lever member, an actuator is at a second end of the first lever member, the second handle is at a first end of a second lever member, and moving the first and second handles from the open position to the closed position causes movement of the actuator, which causes movement of the second jaw member from the retracted position to the extended position.

30. The method of claim 29, wherein the actuator is in contact with a contact portion of a rod at a first end of the rod, and the second jaw member is at a second end of the rod.

31. The method of claim 30, wherein movement of the second jaw member from the retracted position to the extended position is in a direction of a longitudinal axis of the rod.

* * * * *